(12) United States Patent
Dunbar et al.

(10) Patent No.: US 7,066,967 B2
(45) Date of Patent: Jun. 27, 2006

(54) HAIR COLORING COMPOSITIONS AND THEIR USE

(75) Inventors: James Charles Dunbar, Morrow, OH (US); Delyth Angharad James, Pembrokeshire (GB)

(73) Assignee: The Procter & Gamble Company, Cincinnati, OH (US)

(*) Notice: Subject to any disclaimer, the term of this patent is extended or adjusted under 35 U.S.C. 154(b) by 38 days.

(21) Appl. No.: 10/764,191

(22) Filed: Jan. 23, 2004

(65) Prior Publication Data

US 2004/0148713 A1    Aug. 5, 2004

Related U.S. Application Data

(63) Continuation of application No. PCT/US02/23196, filed on Jul. 19, 2002.

(30) Foreign Application Priority Data

Jul. 24, 2001    (GB)    .................. 0118030.6

(51) Int. Cl.
    *A61K 7/13*    (2006.01)

(52) U.S. Cl. .................. 8/405; 8/406; 8/408; 8/410; 8/607

(58) Field of Classification Search .............. 8/405, 8/406, 408, 409, 410, 607
    See application file for complete search history.

(56) References Cited

U.S. PATENT DOCUMENTS

| | | | |
|---|---|---|---|
| 3,561,912 A * | 2/1971 | Karl-Josef et al. ............ | 8/409 |
| 5,520,706 A | 5/1996 | Samain et al. ................. | 8/406 |
| 5,578,087 A * | 11/1996 | Audousset et al. ............ | 8/409 |
| 6,379,396 B1 | 4/2002 | Audousset ..................... | 8/405 |
| 2002/0002747 A1 | 1/2002 | De La Mettrie ............... | 8/405 |
| 2002/0010967 A1 | 1/2002 | De La Mettrie ............... | 8/405 |

FOREIGN PATENT DOCUMENTS

| | | |
|---|---|---|
| EP | 0079540 A | 5/1983 |
| EP | 1040818 A1 | 3/1999 |
| EP | 0951900 A | 10/1999 |
| JP | 2001055316 A | 2/2001 |
| JP | 2001151650 A | 6/2001 |
| WO | WO 98/52519 * | 11/1998 |
| WO | WO 98/52520 * | 11/1998 |
| WO | WO 98/52521 * | 11/1998 |
| WO | WO 98/52522 * | 11/1998 |
| WO | WO 98/52523 * | 11/1998 |
| WO | WO-01/41716 A | 6/2001 |

* cited by examiner

*Primary Examiner*—Eisa Elhilo
(74) *Attorney, Agent, or Firm*—Michael J. Sambrook; Brian M. Bolam; Tara M. Rosnell

(57) ABSTRACT

The present invention provides a hair coloring composition comprising
(iv) at least one developer selected from amino aromatic systems capable of being oxidised and thereafter undergoing only a single electrophilic attack reaction, and
(v) at least one developer selected from amino aromatic systems capable of being oxidised and thereafter undergoing at least two electrophilic attack reactions, and
(vi) at least one coupler,
which delivers improved root-to-tip evenness and improved hair color.

11 Claims, No Drawings

HAIR COLORING COMPOSITIONS AND THEIR USE

CROSS REFERENCE TO RELATED APPLICATION

The application is a continuation of International application PCT/US02/23196 (Case CM2596M) filed on Jul. 19, 2002.

This invention relates to new compositions for colouring hair and to methods of using the compositions in hair colouring processes. In particular it relates to new combinations of developer components and their use for achieving particular effects.

Hair colouring compositions generally comprise various aromatic compounds, commonly known as developers (also known as precursors or primary intermediates), together with various other compounds, commonly known as couplers. These are referred to as oxidative hair colouring agents because they require an oxidising agent for formation of colour. The compounds described as developers are those which react with oxidising agent to form a reactive oxidised intermediate. This intermediate then reacts with the coupler or couplers to give a coloured molecule. Some developers are capable of reacting with another molecule of the same type, ie self-coupling. Couplers do not generally react with oxidising agent but instead react with the reactive oxidised intermediate formed by reaction between the developer and the oxidising agent.

In our earlier publications WO98/52591, WO98/52520, WO98/52521, WO98/52522 and WO98/52523 we describe hair colouring compositions which use defined types of oxidative hair colouring agents. In particular, in these publications it is essential that the couplers are selected from three groups (A), (B) and (C), which give cyan, yellow and magenta colours respectively when they couple with a defined developer. In these publications, the developer must be of a type which is capable of being oxidised and thereafter undergoing only a single electrophilic attack. The preferred and exemplified compositions contain only these defined developers and couplers, although it is acknowledged that other types of oxidative hair colouring agent may additionally be present.

Other publications which disclose developers of this general type (single electrophilic attack developers) include EP-A-079,540, which discloses 2,6-dichloro-para-aminophenol as developer in combination with various couplers, but no further developers, and EP-A-951,900, which includes 2,6-dichloro-para-aminophenol as an essential component and exemplifies it together with various couplers and other single electrophilic attack developers.

We have found that although compositions containing single electrophilic attack developers give benefits in terms of accuracy of prediction of final colour, they can exhibit problems with evenness of colouration. In particular, in hair that has previously been coloured and/or bleached and/or permed the condition of the root hair is often different from the condition of the hair at the tip. Evenness of colouration from root to tip can thus be unsatisfactory. It would be desirable to improve this, whilst maintaining or improving the colour applied to the hair.

According to the invention we provide a hair colouring composition comprising
(i) at least one developer selected from amino aromatic systems capable of being oxidised and thereafter undergoing only a single electrophilic attack reaction, and
(ii) at least one developer selected from amino aromatic systems capable of being oxidised and thereafter undergoing at least two electrophilic attack reactions, and
(iii) at least one coupler.

We find that the use of a combination of a developer capable of being oxidised and thereafter undergoing only a single electrophilic attack reaction (single electrophilic attack developer) and a developer capable of being oxidised and thereafter undergoing at least two electrophilic attack reactions (multiple electrophilic attack developer) surprisingly provides improved root-to-tip evenness over compositions containing only single electrophilic attack developers and can also provide improved root-to-tip evenness in comparison with compositions containing multiple electrophilic attack developers alone. It also provides an improved colour quality.

Accordingly, the invention also provides the use of a composition comprising (i) single electrophilic attack developer and (ii) multiple electrophilic attack developer and (iii) coupler to improve the root-to-tip evenness of colour applied to hair. In particular, it provides the use of multiple electrophilic attack developer to improve the root-to-tip evenness provided by a hair colouring composition comprising single electrophilic attack developer and coupler.

The compositions of the invention may be used in a method of colouring hair. The invention also provides a kit comprising a separately packaged colouring component containing single electrophilic attack developer and multiple electrophilic attack developer and coupler and a separately packaged oxidising component, which may be used to provide compositions for colouring hair.

In the invention it is essential that at least two different types of developer are used. Developers are those components of the composition which react with the oxidising agent to form a reactive intermediate which then goes on to react with the couplers.

The first developer is capable of being oxidised and thereafter undergoing only a single electrophilic attack. Preferably it is selected from para- and ortho-disubstituted benzene compounds, wherein one of the substituents is a primary amine group and the other substituent is a different group, preferably selected from nitro, hydroxyl or disubstituted amine. Preferably it is selected from substituted and unsubstituted paraaminophenols. Paraaminophenol itself may be used, as may be dihaloparaaminophenols, where halo can be chloro or bromo. In particular especially good results are given by 2,6-dichloroparaaminophenol.

The composition also contains a multiple electrophilic attack developer. This may be selected from para- and ortho-disubstituted benzene compounds, disubstituted pyridine compounds, disubstituted pyrimidines and diamino substituted pyrazoles. Diamino benzenes and diaminopyrazoles for example 1-(2 hydroxyethyl)4,5-diaminopyrazole are preferred.

We observe particularly good improvements in root-to-tip evenness with paraphenylenediamine.

We believe that beneficial results can be achieved by the use of a multiple electrophilic attack developer which can undergo self-coupling, ie the reactive oxidised intermediate formed by oxidation of one developer molecule may undergo reaction with a second developer molecule of the same type.

Suitable amounts of total developer are from 0.01 to 5 or 7 wt. % based on total composition applied to the hair. Preferred amounts are from 0.3 to 2 or 4%, preferably 0.4 to 1.5 or 3%.

Generally the ratio of single electrophilic attack developer to multiple electrophilic attack developer can be for instance from 5:95 to 95:5, in particular 20:80 to 80:20, preferably 60:40 to 40:60.

The composition also comprises a coupler. A coupler reacts with the reactive intermediate formed by oxidation of the developer. Generally it does not itself react with the oxidising agent under the conditions used in the hair colouring process.

The couplers may be of the types discussed in WO98/52522.

For instance, couplers which give a cyan colour reaction with the developers may be selected from compounds of the formula I:

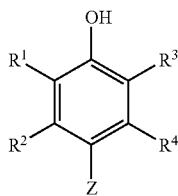

in which Z is H or another active leaving group. Preferably Z is H.

$R^1$, $R^2$, $R^3$ and $R^4$ are, independently, H, OH, —$CH_2H$, —$CO_2R$, F, Cl, Br, —CN, —$NO_2$—, $CF_3$, cycloalkyl, alkenyl, cycloalkenyl, aryl, alkaryl, aralkyl, —NH2, —NHR, —NHCOR, —$NR_2$, —NHCOR, —R'NHCOR, —CONHR, R'CONHR, —R'OH, —$SO_2R$, $SO_2NHR$, —$R'SO_2R$, —$R'SO_2R$, —$R'SO_2NHR$, —$SO_3H$, —OR, —R'OR or —COR, in any of which R is H, alkyl, cycloalkyl, alkenyl, cycloalkenyl, aryl, alkaryl or aralkyl, and R' is alkylene, alkenylene, cycloalkylene, cycloalkenylene, arylene, alkarylene or aralkylene, or substituted versions of any of these. Additionally, $R^1$ and $R^2$ may together form a substituted or unsubstituted cycloalkyl, cycloalkenyl or aryl group. Substituting groups include OH, —OR, Cl, Br, F, —$CO_2H$, —$CO_2R$, —$NH_2$ and —COR.

They may thus be selected from phenol and naphthol compounds having an active leaving group para to the hydroxyl group. The active leaving group Z is any group which can be removed under the conditions prevailing during a hair colouring process so that the reactive oxidised intermediate formed by oxidation of the developer reacts at that position in the coupler molecule. A bond between the coupler and developer molecule is thus formed at the site of the active leaving group. Examples of active leaving groups are H, PhO, Cl, Br, alkoxy (RO) such as phenoxy PhO, and RS— in which R is alkyl or aryl, but any leaving group which leaves during the reaction so as to allow coupling between the reactive intermediate formed from the developer and the coupler is suitable. A preferred compound is 1-acetoxy-2-methylnaphthalene.

The cyan couplers may be used in relatively low amounts, for instance 0.001 to 1%, preferably 0.004 or 0.00 to 0.5%, for instance not more than 0.05%, all percentages being by weight based on total weight of composition applied to the hair.

The couplers may alternatively be selected from 1,3-diketones of the formula II:

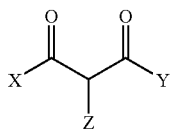

in which X and Y are non-leaving substituents and Z is an active leaving group, such that in the presence of an oxidising agent the or each developer reacts with the or each coupler substantially only at the position having the active leaving group Z. These are of the same general type as disclosed in WO98/52522 as yellow couplers. These couplers produce a yellow colour on reacting with a developer molecule.

Each of X and Y may be independently H, alkyl, cycloalkyl, alkenyl, cycloalkenyl, aryl, alkaryl aralkyl, —R'NHCOR, —R'CONHR, —ROH, —$R'CO_2R$, —$R'CO_2NHR$, —NHCOR, —$NR_2$, —NHR, —$NH_2$, —R'OR and —RO. In these groups R can be H, alkyl, cycloalkyl, alkenyl, cycloalkenyl, aryl, alkaryl or aralkyl and R' can be alkylene, cycloalkylene, alkenylene, cycloalkenylene, arylene, alkarylene or aralkylene. Substituted versions of any of these can be used. Suitable substituents include OH, —OR, Cl, Br, S—$CO_2H$, —$CO_2R$, —$NH_2$ and —COR.

In the formula II, X and Y are each preferably methyl or ethyl and preferred couplers of the formula II are dimethyl acetoaetamide and diethyl acetoacetamide.

In the formula II the active leaving group Z may be any of the active leaving groups discussed above for the cyan type couplers of the formula I.

Yellow couplers may also be selected from compounds of the formula III:

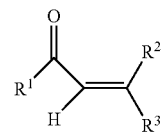

in which $R^1$, $R^2$ and $R^3$ are, independently, cycloalkyl, alkenyl, cycloalkenyl, aryl, alkaryl, aralkyl, —R'NHCOR, —CONHR, —R'CONHR, —R'OH, —$R'CO_2R$, —$R'SO_2NHR$, —R'OR or —COR, in any of which R is H, alkyl, cycloalkyl, alkenyl, cycloalkenyl, aryl, alkaryl or aralkyl and $R^1$ is alkylene, alkenylene, cycloalkylene, cycloalkenylene, arylene, alkarylene or aralkylene or substituted versions of any of these.

Preferred yellow couplers are of the formula II.

The amount of yellow coupler is often from 0.05 to 4 wt. %, eg 0.05 to 3 wt. %, but in some cases is up to 5 or 6%. For instance it may from 0.2 to 3 wt. %, eg 0.2 to 2 wt. % based on weight of composition applied to the hair.

The couplers may also be selected from compounds of the formula IV:

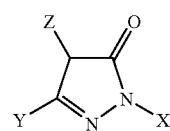

in which X is a non-leaving substituent, and Z is an active leaving group, and Y is an active leaving group or a non-leaving substituent, such that in the presence of an oxidising agent the or each developer reacts with the or each coupler substantially only at the position having the active leaving group Z and, if Y is an active leaving group, Y. Normally Y is a non-leaving substituent. The active leaving groups may be the same as those discussed above for formula I.

X can be H, alkyl, alkenyl, cycloalkyl, cycloalkenyl, aryl, alkaryl, aralkyl, —R'NHCOR, —R'CONHR, —R'OH, —R'SO$_2$R, —R'SO$_2$NHR or —R'OR. Y can be H, —OH, CO$_2$H, —CO$_2$R, F, Cl, Br, —CN, —NO$_2$, CF$_3$, alkyl, cycloalkyl, alkenyl, cycloalkenyl, aryl, alkaryl, aralkyl, —NH$_2$, —NHR, NR$_2$, —NHCOR, —R'NHCOR, —CONHR, —R'CONHR, NHCONHR, —R'OH, —SO$_2$R, —SO$_2$NHR, —R'SO$_2$R, —R'SO$_2$NHR, —SO$_3$H, —OR, —R'OR or —COR. In all of these, R can be H, alkyl, cycloalkyl, alkenyl, cycloalkenyl, aryl, alkaryl or aralkyl, and R' can be alkylene, cycloalkylene, alkenylene, cycloalkenylene, arylene, alkarylene or aralkylene (or substituted versions of any of these). Suitable substituting groups include —OH, —OR, Cl, Br, F, —CO$_2$H, —CO$_2$R, —NH$_2$ and —COR.

These couplers are of the same general type as disclosed in WO98/52522 and give a magenta colour on reaction with the reactive oxidised intermediate formed by reaction of developer molecule and oxidising agent.

Preferably Y is selected from phenyl and —NHCOR in which R is alkyl. More preferably Y is selected from phenyl and N-acetyl.

In preferred coupler compounds X is methyl and Y is phenyl; X is phenyl and X is NHCOR, preferably N-acetyl; X is methyl and Y is NHCOR, preferably N-acetyl; X is methyl or phenyl and X is NHCOPhNH$_2$; X is phenyl and Y is phenyl.

Couplers of this type can be used in amounts of from for instance 0.01 to 4%, preferably 0.01 to 2%, more preferably 0.03 to 3, eg 0.03 to 2%, and in some compositions not more than 1 or 0.5%.

The couplers may be selected from conventional coupler compounds, in particular disubstituted benzene compounds, especially meta-disubstituted benzene compounds.

Total levels of developer and coupler generally vary according to the shade required. For blonde shades amounts of from 0.001 to 4 wt. % are preferred. For red shades amounts of 0.001 to 4 wt. % are preferred. For brown shades amounts of 0.01 to 4% are preferred. For black shades amounts of 0.1 to 4 wt. % are preferred.

The compositions may be used in methods of colouring hair. In these methods it is generally necessary to include an oxidising agent in the composition just before it is applied to the hair. Normally the composition of the invention will be supplied in at least two individual packages such as bottles, the oxidising agent being included in one package and the developers being included in another.

A preferred oxidising agent is hydrogen peroxide. This is often used in amounts up to 10 wt. %, based on weight of composition applied to the hair. Other oxidising agents which may be used include other inorganic peroxygen oxidising agents, preformed organic peroxyacid oxidising agents and other organic peroxides such as urea peroxide, melamine peroxide, and mixtures of any of these.

Suitable oxidising agents are preferably water-soluble, that is they have a solubility of at least about 5 g in 1,000 ml of deionised water at 25° C. ('Chemistry' C. E. Mortimer, 5th Edition, page 277).

Usually the colouring compositions of the invention have pH above 7, in particular above pH 8 or 9. A pH of from 9 to 12 is often suitable. The systems of the invention can also be incorporated into low pH (eg pH 1 to 6) hair colouring systems.

In practice the composition of the first aspect of the invention may be supplied to the consumer as a single package containing developer and coupler in a single unit such as a bottle.

It is also possible to supply the composition so that the developers are individually packaged and the couplers are individually packaged. Couplers may be supplied as a preformed mixture selected to give a particular colour. Alternatively they can be supplied separately for mixing by the consumer to give a variety of different hair colours.

In all cases, the essential components are mixed to form the composition of the invention before application to the hair.

Generally oxidising agent is individually packaged separately from any of the colouring components. It is often mixed with these to form a component of the hair colouring composition before application to the hair. Alternatively it can be applied to the hair separately either before or after the hair colouring composition.

The developers, couplers and oxidising agent, and any other materials to be applied to the hair as components of the composition of the invention, may be provided in any suitable physical form. A preferred physical form is liquid. The liquid may be of low viscosity, for instance it may be water thin, or it may be of higher viscosity. The material may be suspended in a gel network. The gel may be solid or of low viscosity.

The materials for colouring the hair are often formulated so that when they are mixed to form the composition of the invention for application to the hair they form a product of cream-like consistency, which is convenient for application to the hair. The final composition which is applied to the hair is often in the form of an emulsion.

Each individual material may be supplied in a form such that the composition containing it has a pH of above or below 7. For instance it may be from pH 1 to 11. In order to assist solubility of the various components, particularly developers and couplers, in a water-based carrier, the carrier may have a pH of above 6.1 or 6.5 or even above 7, for instance from pH 8 or 9 to pH 10 or 11. A pH as supplied of from 1 to 6 can assist in improving stability of the components.

The materials may be provided such that the pH of the final composition when mixed for application to the hair has a pH below 7 even though one of the components used to form it has a pH of above 7. Alcohols such as ethanol in amounts of from for instance 5 to 10 or 25% may be included to aid solubility of the developers and, particularly, the couplers in a water-based carrier.

The compositions may contain other optional ingredients. These can include other oxidative and non-oxidative colouring agents, buffering agents, hair swelling agents, catalysts for the oxidising agent, thickeners, diluents, enzymes, surfactants (especially anionic amphoteric, non-ionic or zwitterionic surfactants), proteins and polypeptides and derivatives thereof; water-soluble or solubilizable preservatives; dye removers; H$_2$O$_2$ stabilisers; moisturising agents; solvents; anti-bacterial agents; low temperature phase modifiers; viscosity control agents; hair conditioning agents; enzyme stabilisers; TiO$_2$ and TiO$_2$-coated mica; perfumes and perfume solubilizers; chelating agents. Other optional materials include anti-dandruff actives such as ZPT. Details of suitable optional ingredients can be found in WO98/52522.

EXAMPLES

In the following examples various standard tests are used as follows.

I Assessment of Initial Colour and Colour Change (Measurement of ΔE)

The equipment used to measure both the initial colour and colour change of substrates (hair/skin) dyed with colouring compositions of the present invention is a Hunter Colourquest spectrophotometer. The value used to express the degree of colour change on any particular substrate is Delta E (ΔE). Delta E, as defined herein, is represented by a factual sum of L, a, and b values such that:

$$\Delta E = (\Delta L^2 + \Delta a^2 + \Delta b^2)^{1/2}$$

and L is measure of lightness and darkness (colour intensity), wherein L=100 is equivalent to white, and L=0 is equivalent to black. Further, a is a measure of the red and green quotients (colour hues) such that positive equates to red and negative to green and b is a measure of the yellow and blue quotients (colour hues) such that positive equates to yellow and negative equates to blue.

Hunter Colourquest measurements can be carried out on the Hunter Labscan Colourimeter which is a full scanning spectrocolorimeter with a wavelength of from 400–700 nanometers which records the colour of test hair switches (tresses) in terms of L, a and b values. The machine is set to: mode—0/45; port size—1 inch; view size—1 inch; light—D65; field of view—10; UV lamp/filter—none. The hair is placed in a sample holder designed to hold the hair in uniform orientation during measurement. Equivalent calorimeters can be used, but it must be ensured that the hair does not move during measurement. The hair must be spread to cover the 1 inch port during colour measurement. Dots are placed on the switch holder to guide the positioning of the holder at the port. The dots are lined up with a mark on the port and readings are taken at each spot.

Eight measurements are run per switch, 4 on each side, and three switches are run per treatment.

II Hair Switch Colouring Method

To colour hair, a 4 gramme switch of about 8 inch long hair (or a 2 gramme switch of 4 inch long hair) is hung over a suitable container. The test colouring product is then prepared (ie, where applicable the separate bottle components are mixed together) and about 2 grammes of product per gramme hair is applied directly to the test hair switch. The colourant is massaged through the hair switch for up to about 1 minute and then left on the hair switch for up to about 30 minutes. After rinsing with running water for about 1 or 2 minutes the coloured hair switch is then cleansed (according to the shampoo protocol IV below) and dried. Drying can be effected either naturally (without heat assistance) or using a drier. The colour development (initial colour) of the coloured, cleansed, dried test hair switch can then be assessed using the Hunter Colourquest spectrophotometer.

III Hair Switch Cleansing Method

A 4 gramme, 8 inch test switch (or a 2 gramme, 4 inch test switch) of coloured hair is clamped over a suitable container and rinsed thoroughly for about 10 seconds using warm water (at about 100° F. at about 1.5 gallons/minute pressure). Shampoo (about 0.1 ml non-conditioning shampoo per gramme hair) can then be applied directly to the wet test switch using a syringe. After lathering the hair for about 30 seconds the hair is rinsed in running water for about 30 seconds. The shampoo and lathering process is then repeated with a final 60 second rinse. Excess water can be removed (squeezed) from the test switch using the fingers. The test switch is then dried either naturally, or using a pre-heated dryer box at about 140° F. (for about 30 minutes).

IV Bleaching Protocol

Switches of virgin yak hair are bleached using the commercially available bleach Clairol 'Born Blond (with camomile'). This is mixed according to the instructions and 10 grams of the material is applied to each switch and massaged in thoroughly. Each switch is wrapped loosely in clingfilm and left for 30 minutes. It is subsequently rinsed for 2 minutes in tap water at 37° C. It is then shampooed once.

V Evenness Testing

In each test three switches of virgin yak hair are coloured according to the protocol above. Comparison switches are bleached three times according to the bleaching protocol above and subsequently coloured. Delta E values are measured for each set of hair switches and the difference between the average Delta E value for the virgin switches and the Delta E value for the three-times bleached switches is noted as the evenness value.

VI Emulsion Base Formulations

The emulsion base formulation was as follows:

| Component | % w/w in Use |
| --- | --- |
| Water | To 100% |
| Ceteareth 25 | 0.5400 |
| Cetyl Alcohol | 0.8100 |
| Stearyl Alcohol | 1.6300 |
| Sodium Benzoate | 0.0557 |
| Phenoxyethanol | 0.0668 |
| Benzyl Alcohol | 0.0668 |
| Steareth 2 | 0.2700 |
| Tetrasodium EDTA | 0.0223 |
| Di-PEG-2 Soyamine IPDI | 0.2115 |
| Dihydroxyethyl Soyamine Dioleate (Lowenol S216 from Lowenstein) | 2.1150 |
| DC Q2-8220 from Dow Corning | 1.5000 |

An example Emulsion Base making method is given below.
1. Add water to vessel. Heat to above the melt temperature of the fatty alcohols with agitation.
2. Add Fatty Alcohols and Ethoxylated Fatty Alcohols, ie Ceteareth-25, Cetyl alcohol, Stearyl alcohol and Steareth-2, and allow to melt. Increase agitation.
3. Add other surfactants, ie Dihydroxyethyl Soyamine Dioleate (Lowenol S216) and di-PEG-2 soyamine IPDI.
4. Continue mixing with shear.
5. Begin cooling with shear adding preservatives (sodium benzoate, phenoxyethanol, benzyl alcohol) at appropriate temperature.
6. During cooling add silicone containing conditioning agent (DC Q2-8220) with mixing. Mix until homogeneous.
7. Cool to room temperature.

Example 1

The example composition contained (amounts are percentages in the composition finally applied to the hair switches) 0.4% 2, 6-dichloro-para-aminophenol (DCP) as the single electrophilic attack developer, 0.4% paraphenylene diamine (PPD) as the multiple electrophilic attack developer and 1.2% 3-acetamido phenol (3AP) as a cyan coupler. An emulsion base having the composition given above was mixed with the colouring components, which had been formed into a colour premix by pre-dissolving in water (with warming to aid dissolution if necessary) with 0.1% EDTA as chelant, 0.1% ascorbic acid and 0.1% sodium sulfite as antioxidants, and 1.23% ammonium acetate as buffer, all amounts being based on the composition finally applied to the hair. The amount of emulsion base in the composition applied to the hair was 49%. Ammonium hydroxide was added to give a final pH of 10 (the amount was 1.8% based on the composition finally applied to the hair). This mixture was then mixed with 36% hydrogen peroxide in an amount such that the composition finally applied to the hair contained 3% hydrogen peroxide, before application to the hair switches.

Evenness results were as follows:
Composition 1 (DCP plus 3AP) 6.70
Composition 2 (PPD plus 3AP) 5.00
Composition 3 (DCP plus PPD plus 3AP) 2.65.

Thus the combination of two developers gave better root-to-tip evenness than either one of the developers used alone with the same coupler.

Furthermore, the colours produced by composition 3 were beneficial. The colour from composition 1 had a green colour on the hair. Composition 2 gave a very dark blue/black colouration, with the blue hue tending to be drowned out. Composition 3 gave a satisfactory vibrant blue/black colour.

Example 2

In this example the same single electrophilic attack developer and multiple electrophilic attack developer were used as in example 1. The coupler was a magenta coupler, 3-(N-acetyl)amino-1-phenol-2-pyrazolin-5-one (NAPP). Compositions having the same components in the same amounts as Example 1 except that the magenta coupler replaces the cyan coupler of Example 1 were applied to hair. Root to tip evenness values were as follows:
Composition 4: (DCP plus NAPP) 13.47
Composition 5: (PPD plus NAPP) 2.44
Composition 6: (DCP plus PPD plus NAPP) 5.36.

Thus it can be seen that composition 6 of the invention gives significantly improved eveness in comparison with composition 4.

Furthermore, the colours obtained are beneficial. Composition 4 gave a very pink/magenta colour, which is not consumer preferred. Composition 5 appeared very dark violet, again with the magenta hue drowned out. Composition 6 gave a satisfactory vibrant violet/magenta colour.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A hair coloring composition comprising:
  (i) at least one developer of 2,6-dihalo-para-aminophenol and optionally at least one developer selected from aromatic systems capable of being oxidized and thereafter undergoing only a single electrophilic attack reaction;
  (ii) at least one developer of para-phenylenediamine and optionally at least one developer selected from aromatic systems capable of being oxidized and thereafter undergoing at least two electrophilic attack reactions and
  (iii) at least one coupler of 3-acetamidophenol and optionally at least one coupler selected from the group consisting of diketone compounds, pyrazole compounds and the compounds of the following formula;

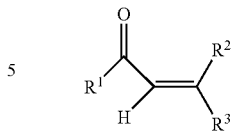

in which $R_1$, $R_2$ and $R_3$ are, independently selected from, cycloalkyl, alkenyl, cycloalkenyl, aryl, alkaryl, aralkyl, —R'NHCOR, —CONHR, —R'CONHR, —R'OH, —R'SO$_2$R, —R'SO$_2$NHR, —R'OR or —COR, in any of which R is H, alkyl, cycloalkyl, alkenyl, cycloalkenyl, aryl, alkaryl or aralkyl and R' is alkylene, alkenylene, cycloalkylene, cycloalkenylene, arylene, alkarylene or aralkylene, or substituted versions of any of these; or mixtures thereof.

2. The composition according to claim 1 in which the developer (i) 2,6-dichloropara-aminophenol.

3. The composition according to claim 1 in which the developer (ii) further selected from the group consisting of disubstituted pyridine compounds, disubstituted pyrimidines, diamino substituted pyrazoles, and mixtures thereof.

4. The composition according to claim 1 in which the developer (ii) is capable of being oxidised and thereafter undergoing self-coupling.

5. The composition according to claim 1 in which the coupler (iii) further selected from the group consisting of 1,3-diketones of the following formula;

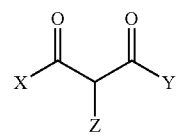

in which X and Y are non-leaving substituents and Z is an active leaving group, such that in the presence of an oxidising agent the developer reacts with the coupler substantially only at the position having the active leaving group Z.

6. The composition according to claim 1 in which the coupler comprises at least one coupler selected from compounds of the following formula:

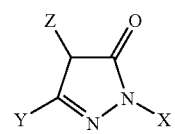

in which X is a non-leaving substituent, and Z is an active leaving group, and Y is an active leaving group or a non-leaving substituent, such that in the presence of an oxidising agent the developer reacts with the coupler substantially only at the position having the active leaving group Z and, if Y is an active leaving group, Y.

7. A method of increasing the root-to-tip evenness of colour applied to hair, said method comprising the step of applying to the hair a composition according to claim 1.

8. The method according to claim 7 in which said hair is selected from the group consisting of previously coloured hair, previously bleached hair, previously permed hair, and combinations thereof.

9. A method of colouring hair comprising applying to the hair (i) at least one developer of 2,6-dihalo-para-aminophenol and optionally at least one or more developers selected from amino aromatic systems capable of being oxidised and thereafter undergoing only a single electrophilic attack reaction and (ii) at least one developer of para-phenylenediamine and optionally at least one or more developers capable of being oxidised and thereafter undergoing at least two electrophilic attack reactions and (iii) at least one coupler of 3-acetamidophenol and optionally at least one coupler selected from the group consisting of diketone compounds, pyrazole compounds and the compounds of the following formula;

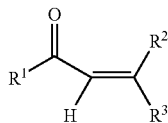

in which $R_1$, $R_2$ and $R_3$ are, independently selected from, cycloalkyl, alkenyl, cycloalkenyl, aryl, alkaryl, aralkyl, —R'NHCOR, —CONHR, —R'CONHR, —R'OH, —R'SO$_2$R, —R'SO$_2$NHR, —R'OR or —COR, in any of which R is H, alkyl, cycloalkyl, alkenyl, cycloalkenyl, aryl, alkaryl or aralkyl and R' is alkylene, alkenylene, cycloalkylene, cycloalkenylene, arylene, alkarylene or aralkylene, or substituted versions of any of these; or mixtures thereof.

10. The method according to claim 9 in which an oxidizing agent is mixed with said one or more developers (i) and (ii) before they are applied to the hair.

11. A hair colouring kit comprising
(a) an individually packaged colouring component comprising (i) at least one developer of 2,6-dihalo-aminophenol and optionally at least one or more developers selected from amino aromatic systems capable of being oxidised and thereafter undergoing only a single electrophilic attack reaction and (ii) at least one developer of para-phenylenediamine and optionally at least one or more developers selected from amino aromatic systems capable of being oxidised and thereafter undergoing at least two electrophilic attack reactions and (iii) at least one coupler of 3-acetamidophenol and optionally at least one coupler selected from the group consisting of diketone compounds, pyrazole compounds of the formula;

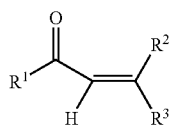

in which $R_1$, $R_2$ and $R_3$ are, independently selected from, cycloalkyl, alkenyl, cycloalkenyl, aryl, alkaryl, aralkyl, —R'NHCOR, —CONHR, —R'CONHR, —R'OH, —R'SO$_2$R, —R'SO$_2$NHR, —R'OR or —COR, in any of which R is H, alkyl, cycloalkyl, alkenyl, cycloalkenyl, aryl, alkaryl or aralkyl and R' is alkylene, alkenylene, cycloalkylene, cycloalkenylene, arylene, alkarylene or aralkylene, or substituted versions of any of these; or mixtures thereof, and
(b) an individually packaged oxidising component.

* * * * *